(12) United States Patent
Kaneko et al.

(10) Patent No.: US 6,858,692 B2
(45) Date of Patent: Feb. 22, 2005

(54) FLUORINATED COMPOUND, FLUOROPOLYMER AND PROCESS FOR ITS PRODUCTION

(75) Inventors: Isamu Kaneko, Kanagawa (JP); Yoko Takebe, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/637,504

(22) Filed: Aug. 11, 2003

(65) Prior Publication Data

US 2004/0132940 A1 Jul. 8, 2004

Related U.S. Application Data

(63) Continuation of application No. PCT/JP02/00796, filed on Jan. 31, 2002.

(30) Foreign Application Priority Data

Feb. 9, 2001 (JP) ........................... 2001-034022
Jul. 19, 2001 (JP) ........................... 2001-219569

(51) Int. Cl.$^7$ ............................................. C08F 136/16
(52) U.S. Cl. ....................... 526/252; 525/215; 525/221; 525/222; 526/253; 570/136
(58) Field of Search ................. 526/252, 253; 525/215, 221, 222; 570/136

(56) References Cited

U.S. PATENT DOCUMENTS 6,310,142 B1 * 10/2001 Apostolo et al.

FOREIGN PATENT DOCUMENTS

| EP | 1365290 A1 | * | 4/2003 |
| JP | 63-238115 | * | 10/1988 |
| JP | 1-168630 |   | 7/1989 |
| JP | 4-59804 |   | 2/1992 |
| JP | 4-59804 A | * | 2/1992 |
| JP | 4-66905 |   | 3/1992 |
| JP | 4-189802 |   | 7/1992 |
| JP | 4-189802 A | * | 7/1992 |
| JP | 4-189880 |   | 7/1992 |
| JP | 4-189880 A | * | 7/1992 |
| JP | 1302813 A1 | * | 4/2003 |
| JP | 1365290 A1 | * | 11/2003 |
| WO | 0 199 138 |   | 10/1986 |

OTHER PUBLICATIONS

Ito et al., "Polymer Design for 157 nm Chemically Amplified Resists", Proceeding of SPIE, vol. 4345, pp. 273–284, (2001).*

* cited by examiner

Primary Examiner—David W. Wu
Assistant Examiner—Henry S. Hu
(74) Attorney, Agent, or Firm—Oblon, Spivak, McClelland, Maier & Neustadt, P.C.

(57) ABSTRACT

A fluoropolymer having repeating units formed by cyclopolymerization of a functional group-containing fluorinated diene represented by the following formula:

$$CF_2=CR^1\text{-}Q\text{-}CR^2=CH_2 \qquad (1)$$

wherein each of $R^1$ and $R^2$ which are independent of each other, is a hydrogen atom, a fluorine atom, an alkyl group having at most 3 carbon atoms, or a fluoroalkyl group having at most 3 carbon atoms, and Q is a bivalent organic group having a functional group bonded thereto, and a production method which comprises subjecting the above diene to radical polymerization. The polymer has a high Tg and a functional group concentration sufficient to exhibit the characteristics thereof.

8 Claims, No Drawings

FLUORINATED COMPOUND, FLUOROPOLYMER AND PROCESS FOR ITS PRODUCTION

TECHNICAL FIELD

The present invention relates to a novel fluorinated compound, an improved fluorinated cyclic polymer having functional groups and a process for its production.

BACKGROUND ART

As fluoropolymers having functional groups, functional group-containing fluoropolymers are known which are used for fluorinated ion exchange membranes, curable fluorinated resin coating materials, etc. However, they are all basically straight chained polymers, and they are obtainable by copolymerization of a fluoroolefin represented by tetrafluoroethylene with a monomer having a functional group.

Further, a polymer containing functional groups and having a fluorinated alicyclic structure in its main chain, is also known. As a method for introducing functional groups to the polymer having a fluorinated alicyclic structure in its main chain, ① a method of utilizing terminal groups of a polymer obtained by polymerization, ② a method of subjecting a polymer to high temperature treatment to oxidize and decompose side chains or terminals of the polymer to form functional groups, or ③ a method of copolymerizing a monomer having a functional group, if necessary, followed by treatment such as hydrolysis to introduce functional groups, is, for example, known (JP-A-4-189880, JP-A-4-226177 or JP-A-6-220232).

The above-mentioned methods are available as methods for introducing functional groups to a polymer having a fluorinated alicyclic structure in its main chain. However, the method for introducing functional groups by heating the terminal groups of the polymer, has a drawback that the functional group concentration is low, and no adequate characteristics of the functional groups can be obtained. Whereas, by the method for introducing functional groups by copolymerizing a monomer having a functional group, there will be a problem such that if the functional group concentration is increased, the mechanical properties tend to decrease due to a decrease of the glass transition temperature (Tg).

It is an object of the present invention to provide a fluorinated compound or a fluoropolymer which has a high concentration of functional groups to provide adequate characteristics of the functional groups and which brings about no decrease of Tg, and a process for its production.

DISCLOSURE OF THE INVENTION

The present invention is the following invention relating to a fluoropolymer having functional groups or functional group-containing side chain groups directly bonded to fluorinated alicyclic rings.

A fluoropolymer having repeating units formed by cyclopolymerization of a functional group-containing fluorinated diene represented by the following formula:

wherein each of $R^1$ and $R^2$ which are independent of each other, is a hydrogen atom, a fluorine atom, an alkyl group having at most 3 carbon atoms, or a fluoroalkyl group having at most 3 carbon atoms, and Q is a bivalent organic group having a functional group.

The above fluoropolymer is produced by cyclopolymerizing a functional group-containing fluorinated diene represented by the above formula (1) in the presence of radicals, etc. The present invention is also the following invention relating to such a process.

A process for producing a fluoropolymer, which comprises cyclopolymerizing a functional group-containing fluorinated diene represented by the above formula (1).

The fluoropolymer of the present invention can readily be made to be a polymer having a high Tg or can be made to be a polymer having a concentration of functional groups sufficient to exhibit their characteristics.

BEST MODE FOR CARRYING OUT THE INVENTION

By the present invention, it has been made possible to produce a cyclized fluoropolymer having functional groups in side chains of the cyclic structure. Namely, the present invention provides a polymer having repeating units formed by cyclopolymerization of a functional group-containing fluorinated diene represented by the following formula (1), and a process for its production:

wherein each of $R^1$ and $R^2$ which are independent of each other, is a hydrogen atom, a fluorine atom, an alkyl group having at most 3 carbon atoms, or a fluoroalkyl group having at most 3 carbon atoms, and Q is a bivalent organic group having a functional group.

By the cyclopolymerization of the fluorinated diene represented by the formula (1) (hereinafter referred to as the fluorinated diene (1)), the following repeating units (a) to (c) are considered to be formed, and from the results of the spectroscopic analyses, etc., the cyclized polymer of the fluorinated diene (1) is considered to be a polymer having a structure comprising repeating units (a), repeating units (b) or both of them, as the main repeating units. Further, the main chain of this cyclized polymer is meant for a carbon chain constituted by carbon atoms which constitute polymerizable unsaturated bonds (in the case of the fluorinated diene (1), the four carbon atoms which constitute polymerizable unsaturated double bonds).

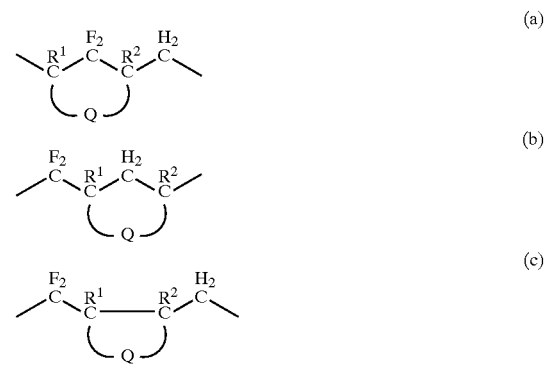

In the formula (1), each of $R^1$ and $R^2$ which are independent of each other, is a hydrogen atom, a fluorine atom, a methyl group or a trifluoromethyl group. $R^1$ is preferably a fluorine atom or trifluoromethyl group. $R^2$ is preferably a hydrogen atom or a methyl group.

Q is not limited to a straight chained structure and may have a side chain structure or a cyclic structure, and its constituting atoms are not limited to carbon atoms and may include hetero atoms such as oxygen atoms, sulfur atoms or nitrogen atoms. In the present invention, the functional groups are meant for groups which provide a desired function, and they may, for example, be ion exchange groups, adhesive groups, cross linkable groups or developable groups.

The shortest distance between both terminal bonds in Q is preferably from 2 to 6 atoms, particularly preferably from 2 to 4 atoms, as represented by number of atoms (hereinafter, the atomic chain constituting this shortest distance will be referred to as the main chain or portion). The atoms constituting the main portion may be composed solely by carbon atoms or may be composed of carbon atoms and other bivalent or higher valent atoms. The bivalent or higher valent atoms other than the carbon atoms, may, for example, be an oxygen atom, a sulfur atom or a nitrogen atom substituted by a monovalent group, particularly preferably an oxygen atom. The oxygen atom, etc., may be present at either one or both of the two terminals, or may be present between carbon atoms in Q.

In the main portion in Q, at least one carbon atom is present, and to the carbon atom constituting the main portion, a functional group or a side chain organic group having a functional group, is bonded. The functional group-containing side chain organic group is preferably a monovalent group. Other than such specific groups, a hydrogen atom or a halogen atom (particularly preferably a fluorine atom) may be bonded to the carbon atom, etc. constituting the main portion, or an alkyl group, a fluoroalkyl group, an alkoxy group, an aryl group or other organic group, may be bonded, and the carbon number of such an organic group is preferably at most 6.

The functional group may, for example, preferably be $OR^3$ (wherein $R^3$ is a hydrogen atom, an alkyl group having at most 5 carbon atoms, an alkoxyalkyl group having at most 8 carbon atoms, or an alkoxycarbonyl group having at most 6 carbon atoms), $COOR^4$ (wherein $R^4$ is a hydrogen atom or an alkyl group having at most 5 carbon atoms), or $SO_2R^5$ (wherein $R^5$ is a halogen atom, a hydroxyl group or an alkoxy group having at most 5 carbon atoms).

As other examples, an amino group, an epoxy group, a trialkoxysilyl group and a cyano group may be mentioned.

The functional group-containing side chain organic group may, for example, be a monovalent organic group such as a functional group-containing alkyl group, a functional group-containing fluoroalkyl group, a functional group-containing alkoxy group, a functional group-containing fluoroalkoxy group or a functional group-containing aryl group. The portion of the functional group-containing side chain organic group, excluding the functional group, preferably has at most 8 carbon atoms, particularly preferably at most 6 carbon atoms.

Q is preferably a bivalent organic group represented by the following formula (3). Accordingly, as the fluorinated diene (1), a compound represented by the following formula (4) is preferred ($R^1$ and $R^2$ are as defined above).

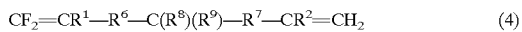

wherein each of $R^6$ and $R^7$ which are independent of each other, is a single bond, an oxygen atom, an alkylene group having at most 3 carbon atoms which may have an etheric oxygen atom, or a fluoroalkylene group having at most 3 carbon atoms which may have an etheric oxygen atom, $R^8$ is a hydrogen atom, a fluorine atom, an alkyl group having at most 3 carbon atoms, or a fluoroalkyl group having at most 3 carbon atoms, and $R^9$ is a functional group or a monovalent side chain organic group having a functional group.

In $R^6$ or $R^7$, the alkylene group is preferably $(CH_2)_m$, and the fluoroalkylene group is preferably $(CF_2)_n$ (wherein each of m and n is an integer of from 1 to 3). In the combination of $R^6$ and $R^7$, it is preferred that both are such groups (in such a case, m+n is preferably 2 or 3), or one of them is such a group, and the other is a single bond or an oxygen atom. In $R^8$, the alkyl group is preferably a methyl group, and the fluoroalkyl group is preferably a trifluoromethyl group.

$R^9$ in the case of a monovalent side chain organic group, is preferably an organic group having at most 8 carbon atoms, wherein the portion excluding the functional group is preferably a hydrocarbon group or a fluorohydrocarbon group. It is particularly preferably a $C_{2-6}$ alkyl group, a $C_{2-6}$ fluoroalkyl group, a phenyl group or a $C_{7-9}$ phenylalkyl group, which has a functional group (provided that in the case of the phenylalkyl group, the functional group is bonded to the phenyl group).

The following compounds may be mentioned as specific examples of the fluorinated diene (1) of the present invention, but the present invention is not limited to such specific examples.

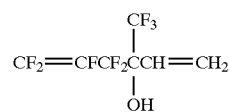

1.

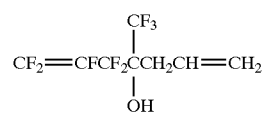

2.

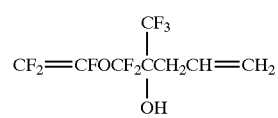

3.

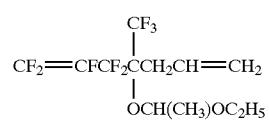

4.

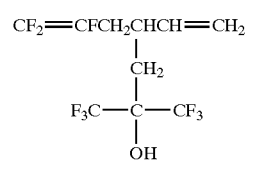

5.

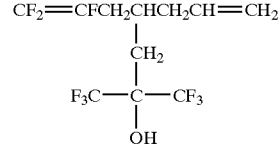

6.

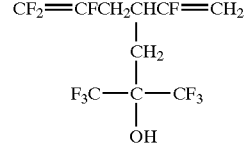

7.

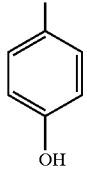

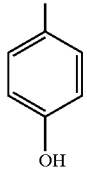

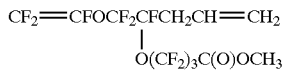

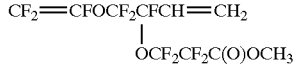

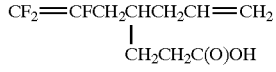

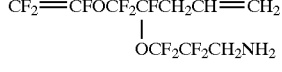

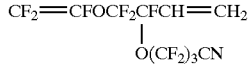

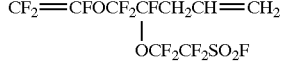

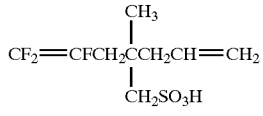

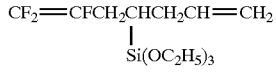

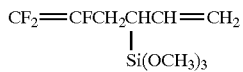

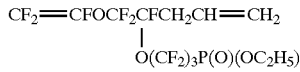

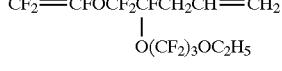

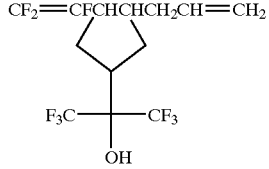

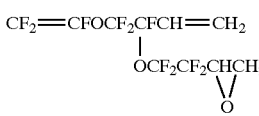

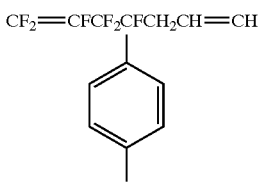

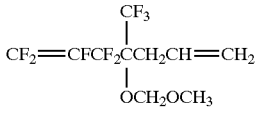

Preferred is a compound represented by the following formula (2):

$$CF_2=CFCF_2C(CF_3)(OR^3)CH_2CH=CH_2 \qquad (2)$$

wherein $R^3$ is a hydrogen atom, an alkyl group having at most 5 carbon atoms, an alkoxyalkyl group having at most 8 carbon atoms, or an alkoxycarbonyl group having at most 6 carbon atoms.

As a particularly preferred example, $CF_2=CFCF_2C(CF_3)(OH)CH_2CH=CH_2$ may be mentioned. Such a specific monomer can be polymerized under a relatively mild condition, whereby a cyclized polymer having functional groups in side chains of the cyclic structure, can be obtained.

The fluoropolymer contains repeating units formed by cyclopolymerization of the fluorinated diene (1), as essential components, but may further contain polymerized units of at least two types of fluorinated dienes (1). Further, within a range not to impair the characteristics, it may further contain monomer units derived from other radical polymerizable monomers. The proportion of such other monomer units is preferably at most 30 mol %, particularly preferably at most 15 mol %.

Such other monomer units may, for example, be monomer units derived from an α-olefin such as ethylene, propylene or isobutylene, a fluorinated olefin such as tetrafluoroethylene or hexafluoropropylene, a fluorinated cyclic monomer such as perfluoro(2,2-dimethyl-1,3-dioxol), a cyclopolymerizable perfluorodiene such as perfluoro(butenyl vinyl ether), an acryl ester such as methyl acrylate or ethyl methacrylate, a vinyl ester such as vinyl acetate, vinyl benzoate or vinyl adamantate, a vinyl ether such as ethyl vinyl ether or cyclohexyl vinyl ether, a cyclic olefin such as cyclohexene, norbornene or norbornadiene, maleic anhydride, or vinyl chloride.

The fluoropolymer of the present invention can be obtained by homopolymerizing or copolymerizing the fluorinated diene (1) in the presence of a polymerization initiating source. The polymerization initiating source is not particularly limited so long as it is capable of letting the polymerization reaction proceed radically, and it may, for example, be a radical-generating agent, light or ionizing radiation. A radical-generating agent is particularly preferred, and it may, for example, be a peroxide, an azo compound or a persulfate.

The polymerization method is also not particularly limited, and it may, for example, be so-called bulk polymerization wherein a monomer is subjected to polymerization as it is, solution polymerization which is carried out in a fluorohydrocarbon, a chlorohydrocarbon, a fluorochlorohydrocarbon, an alcohol, a hydrocarbon or other organic solvent, in which the monomer is dissolved, a suspension polymerization which is carried out in an aqueous medium in the absence or presence of a suitable organic solvent, or emulsion polymerization which is carried out in an aqueous medium in the presence of an emulsifier.

The polymerization temperature and pressure are also not particularly limited, but it is preferred to properly set them taking into consideration various factors such as the boiling point of the monomer, the prescribed heating source, removal of the polymerization heat, etc. For example, a suitable temperature setting can be carried out between 0° C. to 200° C., and practically suitable temperature setting can be carried out within a range of from room temperature to 100° C. Further, the polymerization pressure may be a reduced pressure or an elevated pressure, and practically, the polymerization can properly be carried out within a range of from normal pressure to about 100 atm, preferably from normal pressure to about 10 atm.

The fluoropolymer obtained by the present invention has a cyclic structure in its main chain and has high chemical stability and heat resistance. Yet, functional groups are introduced in the side chains of the cyclic structure, whereby it is possible to exhibit sufficient characteristics of functional groups without bringing about a decrease of Tg, which used to be difficult to accomplish with conventional fluoropolymers. The fluoropolymer of the present invention is useful for e.g. an ion exchange resin, an ion exchange membrane, a fuel cell, various cell materials, a photoresist, an optical fiber, an electronic component, a transparent film material, a covering film for an agricultural green house, an adhesive, a fiber material, a weather-resistant coating material, etc.

EXAMPLES

Now, the present invention will be described in detail with reference to Examples, but it should be understood that the present invention is by no means restricted thereto.

Abbreviations used in the following Examples are as follows.

THF: tetrahydrofuran. PSt: polystyrene. R225: dichloropentafluoropropane (solvent). IPP: diisopropylperoxy dicarbonate.

Preperation Example 1

Preparation of $CF_2$=$CFCF_2C(CF_3)(OH)CH_2CH$=$CH_2$

Into a 2 L glass reactor, 108 g of $CF_2ClCFClCF_2C(O)CF_3$ and 500 ml of dehydrated TFH were put and cooled to 0° C. A diluted solution prepared by diluting 200 ml of a 2M THF solution of $CH_2$=$CHCH_2MgCl$ further with 200 ml of dehydrated THF, was dropwise added thereto in a nitrogen atmosphere over a period of about 5.5 hours. After completion of the dropwise addition, the mixture was stirred at 0° C. for 30 minutes and at room temperature for 17 hours, and 200 ml of 2N hydrochloric acid was dropwise added. 200 ml of water and 300 ml of diethyl ether were added to carry out liquid separation, and a diethyl ether layer was obtained as an organic layer. The organic layer was dried over magnesium sulfate, followed by filtration to obtain a crude liquid. The crude liquid was concentrated by an evaporator and then distilled under reduced pressure to obtain 85 g of $CF_2ClCFClCF_2C(CF_3)(OH)CH_2CH$=$CH_2$ (60 to 66° C./0.7 kPa).

Then, into a 500 ml glass reactor, 81 g of zinc and 170 ml of dioxane were put, and activation of zinc with iodine was carried out. Then, the mixture was heated to 100° C., and a solution prepared by diluting 84 g of $CF_2ClCFClCF_2C(CF_3)(OH)CH_2CH$=$CH_2$ prepared as described above, with 50 ml of dioxane, was dropwise added thereto over a period of 1.5 hours. After completion of the dropwise addition, the mixture was stirred at 100° C. for 40 hours. The reaction solution was subjected to filtration and washed with a small amount of dioxane. The filtrate was distilled under reduced pressure to obtain 30 g of $CF_2$=$CFCF_2C(CF_3)(OH)CH_2CH$=$CH_2$ (36 to 37° C./1 kPa).

NMR spectrum $^1$H—NMR (399.8 MHz, solvent: CDCl$_3$, standard: tetramethylsilane)δ(ppm): 2.74 (d, J=7.3, 2H), 3.54 (broad s, 1H), 5.34 (m, 2H), 5.86 (m, 1H).

$^{19}$F—NMR (376.2 MHz, solvent: CDCl$_3$, standard: CFCl$_3$)δ(ppm): −75.7 (m, 3F), −92.2 (m, 1F), −106.57 (m, 1F), −112.6 (m, 2F), −183.5 (m, 1F).

Example 1

1.0 g of monomer $CF_2$=$CFCF_2C(CF_3)(OH)CH_2CH$=$CH_2$ obtained in the above Preparation Example 1 and 0.5 g of methyl acetate were charged into a glass tube having an inner diameter of 10 mm and a length of 300 mm. Then, 8 mg of perfluorobenzoyl peroxide was added as a polymerization initiator. The interior of the system was freeze-deaerated. Then, the tube was sealed, followed by polymerization for 6 hours in a constant temperature shaking bath (70° C.). After the polymerization, vacuum drying was carried out at 150° C. for 12 hours to remove an unreacted monomer. As a result, 0.9 g of a non-crystalline polymer having a fluorinated cyclic structure in its main chain. The molecular weight measured by GPC employing THF as a solvent and calculated as PSt, was such that the number average molecular weight (Mn) was 43,200, and the weight average molecular weight (Mw) was 233,100, and Mw/Mn= 5.39. Further, Tg measured by the differential scanning calorimetry (DSC) was 154° C., and the polymer was a white powder at room temperature. Further, the 10% weight reduction temperature measured by the thermogravimetry analysis (TGA) was 405° C. The obtained polymer was soluble in acetone, THF, ethyl acetate, methanol and 2-perfluorohexyl ethanol and was insoluble in R225, perfluoro(2-butyltetrahydrofuran) and perfluoro-n-octane.

By $^{19}$F—NMR and $^1$H—NMR, it was confirmed to be a cyclized polymer having at least any one of the following repeating structures.

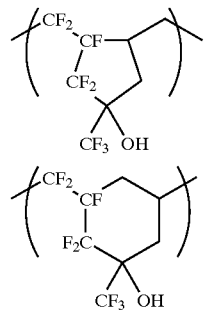

-continued

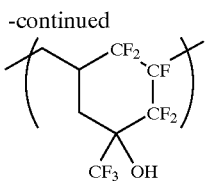

Example 2

The same operation as in Example 1 was carried out by adding 8 mg of IPP as the polymerization initiator and adjusting the polymerization temperature to 40° C., to obtain 0.9 g of a non-crystalline polymer having a fluorinated cyclic structure in its main chain. The molecular weight measured by GPC employing THF as a solvent and calculated as PSt, was such that the number average molecular weight (Mn) was 134,200, and the weight average molecular weight (Mw) was 329,100, and Mw/Mn=2.45. Tg measured by the differential scanning calorimetry (DSC) was 153° C., and it was a white powdery polymer at room temperature. Further, the 10% weight reduction temperature measured by the thermogravimetry analysis (TGA) was 405° C. The obtained polymer was soluble in acetone, THF, ethyl acetate, methanol and 2-perfluorohexyl ethanol and was insoluble in R225, perfluoro(2-butyltetrahydrofuran) and perfluoro-n-octane.

Example 3

Polymerization was carried out in the same manner as in Example 1 using 1.0 g of the monomer obtained in Preparation Example 1, 1.0 g of methyl acetate and 16 mg of perfluorobenzoyl peroxide. After the polymerization, the reaction solution was dropwise added into hexane to repre-cipitate the polymer. Thereafter, vacuum drying was carried out at 150° C. for 12 hours. As a result, 0.8 g of a non-crystalline polymer having a fluorinated cyclic structure in its main chain, was obtained. The molecular weight measured by GPC employing THF as a solvent and calculated as PSt, was such that the number average molecular weight (Mn) was 18,800, and the weight average molecular weight (Mw) was 58,300, and Mw/Mn=3.10. Tg measured by the differential scanning calorimetry (DSC) was 150° C., and it was a white powdery polymer at room temperature. Further, the 10% weight reduction temperature measured by the thermogravimetry analysis (TGA) was 405° C. The obtained polymer was soluble in acetone, THF, ethyl acetate, methanol and 2-perfluorohexyl ethanol and was insoluble in R225, perfluoro(2-butyltetrahydrofuran) and perfluoro-n-octane.

Example 4

10 g of the monomer obtained in Preparation Example 1 and 23 g of methyl acetate were charged into a glass pressure resistant reactor having an internal capacity of 50 cc. Then, 0.24 g of perfluorobenzoyl peroxide was added as a polymerization initiator. The interior of the system was freeze-deaerated, followed by polymerization for 6 hours in a constant temperature shaking bath (70° C.). After the polymerization, the reaction solution was dropwise added into hexane to reprecipitate the polymer. Then, vacuum drying was carried out at 150° C. for 12 hours. As a result, 8 g of a non-crystalline polymer having a fluorinated cyclic structure in its main chain, was obtained. The molecular weight measured by GPC employing THF as a solvent and calculated as PSt, was such that the number average molecular weight (Mn) was 14,200, and the weight average molecular weight (Mw) was 41,300, and Mw/Mn=2.91. Tg measured by the differential scanning calorimetry (DSC) was 148° C., and it was a white powdery polymer at room temperature. Further, the 10% weight reduction temperature measured by the thermogravimetry analysis (TGA) was 405° C. The obtained polymer was soluble in acetone, THF, ethyl acetate, methanol and 2-perfluorohexyl ethanol and was insoluble in R225, perfluoro(2-butyltetrahydrofuran) and perfluoro-n-octane.

Preperation Example 2

Preparation of $CF_2\!=\!CFCF_2C(CF_3)(OCH_2OCH_3)$ $CH_2CH\!=\!CH_2$

Into a 10 L glass reactor, 758 g of $CF_2ClCFClCF_2C(O)$ $CF_3$ and 4.5 L of dehydrated THF were put and cooled to 0° C. 1.4 L of a 2M THF solution of $CH_2\!=\!CHCH_2MgCl$ was dropwise added thereto in a nitrogen atmosphere over a period of about 10.5 hours. After completion of the dropwise addition, the mixture was stirred at 0° C. for 30 minutes and at room temperature for 12 hours. Then, 350 g of chloromethylmethyl ether was dropwise added thereto and further stirred at room temperature for 92 hours. 1.5 L of water was added to carry out liquid separation. The organic layer was concentrated by an evaporator, and the obtained crude liquid was washed twice with 1.5 L of water, followed by distillation under reduced pressure to obtain 677 g of $CF_2ClCFClCF_2C(CF_3)(OCH_2OCH_3)CH_2CH\!=\!CH_2$ (53 to 55° C./0.17 kPa).

Then, into a 3 L glass reactor, 577 g of zinc and 1.3 L of dioxane were put, and activation of zinc with iodine was carried out. Then, the mixture was heated to 100° C., and 677 g of $CF_2ClCFClCF_2C(CF_3)(OCH_2OCH_3)$ $CH_2CH\!=\!CH_2$ prepared as described above, was dropwise added over a period of 2 hours. After completion of the dropwise addition, the mixture was stirred at 100° C. for 47 hours. The reaction solution was subjected to filtration and washed with a small amount of dioxane. To the filtrate, 2.5 L of water and 1.5 L of diethyl ether were added to carry out liquid separation. The organic layer was dried over anhydrous magnesium sulfate, followed by filtration to obtain a crude liquid. The crude liquid was concentrated by an evaporator, followed by distillation under reduced pressure to obtain 177 g of $CF_2\!=\!CFCF_2C(CF_3)(OCH_2OCH_3)$ $CH_2CH\!=\!CH_2$ (43 to 45° C./0.6 kPa).

NMR spectrum $^1$H—NMR (399.8 MHz, solvent: $CDCl_3$, standard: tetramethylsilane)δ(ppm): 3.16 (broad, 2H), 3.44 (s, 3H), 4.95 (m, 2H), 5.22 (m, 2H), 5.92 (m, 1H).

$^{19}$F—NMR (376.2 MHz, solvent: $CDCl_3$, standard: $CFCl_3$)δ(ppm): −72.5 (m, 3F), −92.9 (m, 1F), −106.8 (m, 1F), −109.7 (m, 2F), −183.0 (m, 1F).

Preperation Example 3

Preparation of $CF_2\!=\!CFCF_2C(CF_3)(OH)CH\!=\!CH_2$

Into a 2 L glass reactor, 104 g of $CF_2ClCFClCF_2C(O)CF_3$ and 600 ml of dehydrated THF were put and cooled to 0° C. 370 ml of a 1M THF solution of $CH_2\!=\!CHMgBr$ was dropwise added thereto in a nitrogen atmosphere over a period of 7 hours. After completion of the dropwise addition, the mixture was stirred at 0° C. for 30 minutes and at room temperature for 15 hours, and 200 ml of 2M hydrochloric acid was dropwise added. 200 ml of water and 300 ml of diethyl ether were added to carry out liquid separation, and a diethyl ether layer was obtained as an organic layer. The organic layer was dried over magnesium sulfate, followed by filtration to obtain a crude liquid. The crude liquid was concentrated by an evaporator, followed by distillation under reduced pressure to obtain 80 g of $CF_2ClCFClCF_2C(CF_3)(OH)CH=CH_2$ (43 to 45° C./0.6 kPa).

Then, into a 500 ml glass reactor, 80 g of zinc and 220 ml of dioxane were put, and activation of zinc with iodine was carried out. Then, the mixture was heated to 100° C., and 80 g of $CF_2ClCFClCF_2C(CF_3)(OH)CH=CH_2$ prepared as described above, was dropwise added over a period of 1 hour. After completion of the dropwise addition, the mixture was stirred at 100° C. for 40 hours. The reaction solution was subjected to filtration and washed with a small amount of dioxane. The filtrate was distilled under reduced pressure to obtain 37 g of $CF_2=CFCF_2C(CF_3)(OH)CH=CH_2$ (40 to 42° C./2.4 kPa)

NMR spectrum $^1H$—NMR (399.8 MHz, solvent: $CDCl_3$, standard: tetramethylsilane)δ(ppm): 4.89 (broad s, 1H), 5.71 (m, 1H), 5.96 (m, 2H).

$^{19}F$—NMR (376.2 MHz, solvent: $CDCl_3$, standard: $CFCl_3$)δ(ppm): −74.1 (m, 3F), −91.9 (m, 1F), −106.7 (m, 1F), −113.1 (m, 2F), −182.9 (m, 1F).

Example 5

5 g of the hydroxyl group-containing fluorinated diene obtained in Preparation Example 1 (hereinafter referred to as diene 1), 5.7 g of a fluorinated diene obtained in Preparation Example 2 (hereinafter referred to as diene 2) and 23 g of methyl acetate were charged into a glass pressure resistant reactor having an internal capacity of 50 cc. Then, 0.24 g of perfluorobenzoyl peroxide was added as a polymerization initiator. The interior of the system was freeze-deaerated, followed by polymerization for 6 hours in a constant temperature shaking bath (70° C.). After the polymerization, the reaction solution was dropwise added into hexane to reprecipitate the polymer. Then, vacuum drying was carried out at 150° C. for 12 hours. As a result, 8.5 g of a non-crystalline polymer having a fluorinated cyclic structure in its main chain, was obtained. The composition of monomer units in polymer 15A as measured by $^{19}F$—NMR and $^1H$—NMR was diene 1 units/diene 2 units=52/48 (molar ratio).

The molecular weight of the obtained polymer measured by GPC employing THF as a solvent and calculated as PSt, was such that the number average molecular weight (Mn) was 12,000, and the weight average molecular weight (Mw) was 34,800, and Mw/Mn=2.90. With the above polymer, Tg measured by the differential scanning calorimetry (DSC) was 129° C., and the 10% weight reduction temperature measured by the thermogravimetry analysis (TGA) was 363° C. The above polymer was a white powdery polymer at room temperature, and it was soluble in acetone, THF, ethyl acetate, methanol and 2-perfluorohexyl ethanol and was insoluble in R225, perfluoro(2-butyltetrahydrofuran) and perfluoro-n-octane.

By $^{19}F$—NMR and $^1H$—NMR, it was confirmed to be a cyclized polymer having repeating unit structures similar to the polymer obtained in Example 1.

Example 6

2 g of the fluorinated diene obtained in Preparation Example 2 and 40 g of methyl acetate were charged into a glass pressure resistant reactor having an internal capacity of 100 cc. Then, 0.1 g of perfluorobenzoyl peroxide was added as a polymerization initiator. The interior of the system was freeze-deaerated, followed by polymerization for 16 hours in a constant temperature shaking bath (70° C.). After the polymerization, the reaction solution was dropwise added into hexane to reprecipitate the polymer. Then, vacuum drying was carried out at 150° C. for 12 hours. As a result, 6.1 g of a non-crystalline polymer having a fluorinated cyclic structure in its main chain, was obtained.

The obtained polymer had a Tg of 120° C. as measured by the differential scanning calorimetry (DSC) and was a white powdery polymer at room temperature. Further, with the obtained polymer, the 10% weight reduction temperature measured by the thermogravimetry analysis (TGA) was 390° C., and by $^{19}F$—NMR and $^1H$—NMR, it was confirmed to be a cyclized polymer having repeating structures similar to those in Example 1.

Example 7

10 g of the fluorinated diene obtained in Preparation Example 3 and 22 g of methyl acetate were charged into a glass pressure resistant reactor having an internal capacity of 50 cc. Then, 0.23 g of perfluorobenzoyl peroxide was added as a polymerization initiator. The interior of the system was freeze-deaerated, followed by polymerization for 7 hours in a constant temperature shaking bath (70° C.). After the polymerization, the reaction solution was dropwise added into hexane to reprecipitate the polymer. Then, vacuum drying was carried out at 150° C. for 12 hours. As a result, 8.2 g of a non-crystalline polymer having a fluorinated cyclic structure in its main chain, was obtained.

The molecular weight of the obtained polymer measured by GPC employing THF as a solvent and calculated as PSt, was such that the number average molecular weight (Mn) was 10,000, and the weight average molecular weight (Mw) was 28,000, and Mw/Mn=2.80. The obtained polymer had a Tg of 159° C. as measured by the differential scanning calorimetry (DSC), and was a white powdery polymer at room temperature. Further, the 10% weight reduction temperature measured by the thermogravimetry analysis (TGA) was 395° C. The obtained polymer was soluble in acetone, HTF, ethyl acetate, methanol and 2-perfluorohexyl ethanol and was insoluble in R225, perfluoro(2-butyltetrahydrofuran) and perfluoro-n-octane. By $^{19}F$—NMR and $^1H$—NMR, it was confirmed to be a cyclized polymer having at least either one of the following repeating structures.

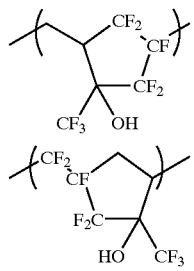

Industrial Applicability

According to the present invention, by subjecting a monomer having two terminal double bonds and a functional group in a side chain of the connecting chain, to radical polymerization, it is possible to smoothly and advantageously obtain the desired cyclized fluoropolymer having functional groups in side chains of the cyclic structure while suppressing side reaction for gelation. The fluoropolymer obtained by the present invention has a cyclic structure in its main chain and has high chemical stability and heat resistance. Besides, functional groups are introduced in the side chains of the cyclic structure, whereby adequate characteristics of the functional groups can be provided without bringing about a decrease of Tg, which used to be difficult to accomplish with conventional fluoropolymers. The fluoropolymer of the present invention is useful for e.g. an ion exchange resin, an ion exchange membrane, a fuel cell, various cell materials, a photoresist, an optical fiber, an electronic component, a transparent film material, a covering film for an agricultural green house, an adhesive, a fiber material, a weather-resistant coating material, etc.

The present application is a continuation of International Application PCT/JP02/00796, filed on Jan. 31, 2002, which is incorporated herein by reference. The entire disclosures, including specifications, claims and summaries, of Japanese Patent Application No. 2001-034022 filed on Feb. 9, 2001 and Japanese Patent Application No. 2001-219569 filed on Jul. 19, 2001, from which the present application claims priority, are incorporated herein by reference in their entirety.

What is claimed is:

1. A fluoropolymer having repeating units formed by cyclopolymerization of a functional group-containing fluorinated diene represented by the following formula:

$$CF_2=CR^1\text{-}Q\text{-}CR^2=CH_2 \qquad (1)$$

wherein each of $R^1$ and $R^2$ which are independent of each other, is a hydrogen atom, a fluorine atom, an alkyl group having at most 3 carbon atoms, or a fluoroalkyl group having at most 3 carbon atoms, and Q is a bivalent organic group having at least one carbon atom in its main chain and having a functional group bonded to a carbon atom of the main chain of Q or having a side chain organic group bonded to a carbon atom of the main chain of Q and having a functional group bonded to the side chain.

2. The fluoropolymer according to claim 1, wherein Q is an alkylene group, an oxyalkylene group, a fluoroalkylene group or an oxyfluoroalkylene group, which has a functional group or a side chain having a functional group, and of which the portion excluding the functional group or the side chain having a functional group, has from 2 to 4 carbon atoms.

3. The fluoropolymer according to claim 1, wherein the functional group is $OR^3$, (wherein $R^3$ is a hydrogen atom, an alkyl group having at most 5 carbon atoms, an alkoxyalkyl group having at most 8 carbon atoms, or an alkoxycarbonyl group having at most 6 carbon atoms), $COOR^4$, (wherein $R^4$ is a hydrogen atom or an alkyl group having at most 5 carbon atoms), or $SO_2R^5$, (wherein $R^5$ is a halogen atom, a hydroxyl group or an alkoxy group having at most 5 carbon atoms).

4. A fluoropolymer according to claim 1 wherein the functional group is at least one member selected from the group consisting of $OR^3$, wherein $R^3$ is a hydrogen atom, an alkyl group having at most 5 carbon atoms, an alkoxyalkyl group having at most 8 carbon atoms, an alkoxycarbonyl group having at most 6 carbon atoms, $COOR^4$, wherein $R^4$ is a hydrogen atom or an alkyl group having at most 5 carbon atoms, $SO_2R^5$, wherein $R^5$ is a halogen atom, a hydroxyl group or an alkoxy group having at most 5 carbon atoms, an amino group, an epoxy group, a trialkoxysilyl group and a cyano group.

5. A process for producing a fluoropolymer, which comprises cyclopolymerizing a functional group-containing fluorinated diene represented by the following formula:

$$CF_2=CR^1\text{-}Q\text{-}CR^2=CH_2 \qquad (1)$$

wherein each of $R^1$ and $R^2$ which are independent of each other, is a hydrogen atom, a fluorine atom, an alkyl group having at most 3 carbon atoms, or a fluoroalkyl group having at most 3 carbon atoms, and Q is a bivalent organic group having at least one carbon atom in its main chain having a functional group bonded to a carbon atom of the main chain of Q or having a side chain organic group bonded to a carbon atom of the main chain of Q and having a functional group bonded to the side chain.

6. A compound represented by the following formula (2):

$$CF_2=CFCF_2C(CF_3)(OR^3)CH_2CH=CH_2 \qquad (2)$$

wherein $R^3$ is a hydrogen atom, an alkyl group having at most 5 carbon atoms, an alkoxyalkyl group having at most 8 carbon atoms, or an alkoxycarbonyl group having at most 6 carbon atoms.

7. A process for producing a fluoropolymer, which comprises cyclopolymerizing the compound represented by formula (2) in claim 6.

8. The fluoropolymer produced by the process of claim 7.

* * * * *